(12) United States Patent
O'Donnell et al.

(10) Patent No.: US 8,940,319 B2
(45) Date of Patent: Jan. 27, 2015

(54) FORMULATIONS, DEVICES AND METHODS FOR TREATING AND PREVENTING MUCOSITIS

(75) Inventors: Francis E. O'Donnell, Longboat Key, FL (US); Angelos M. Stergiou, Athens (GR)

(73) Assignee: Accentia Biopharmceuticals, Inc., Tampa, FL (US)

( * ) Notice: Subject to any disclaimer, the term of this patent is extended or adjusted under 35 U.S.C. 154(b) by 209 days.

(21) Appl. No.: 13/486,197

(22) Filed: Jun. 1, 2012

(65) Prior Publication Data

US 2012/0237618 A1 Sep. 20, 2012

Related U.S. Application Data

(63) Continuation of application No. 12/534,575, filed on Aug. 3, 2009, now Pat. No. 8,211,460, which is a continuation of application No. 12/417,378, filed on Apr. 2, 2009, now abandoned.

(60) Provisional application No. 61/041,866, filed on Apr. 2, 2008.

(51) Int. Cl.
*A61K 33/10* (2006.01)
*A61P 29/00* (2006.01)
*B65D 69/00* (2006.01)
*B65D 85/00* (2006.01)
*A61K 9/00* (2006.01)
*A61K 33/42* (2006.01)
*A61K 45/06* (2006.01)
*A61K 47/02* (2006.01)
*A61K 47/24* (2006.01)
*A61K 9/16* (2006.01)

(52) U.S. Cl.
CPC ............ *A61K 9/0043* (2013.01); *A61K 9/0095* (2013.01); *A61K 33/10* (2013.01); *A61K 33/42* (2013.01); *A61K 45/06* (2013.01); *A61K 47/02* (2013.01); *A61K 47/24* (2013.01); *A61K 9/1611* (2013.01); *A61K 9/1617* (2013.01); *Y10S 514/853* (2013.01)
USPC ............... 424/434; 424/45; 424/46; 424/489; 424/606; 424/687; 514/853

(58) Field of Classification Search
CPC ... A61K 9/0043; A61K 9/0095; A61K 33/10; A61K 33/42; A61K 45/06
USPC .................... 424/434, 45, 46, 489, 606, 687; 514/853
See application file for complete search history.

(56) References Cited

U.S. PATENT DOCUMENTS

| | | | |
|---|---|---|---|
| 6,025,326 A | 2/2000 | Steinberg et al. | |
| 6,207,703 B1 | 3/2001 | Ponikau | |
| 6,291,500 B2 | 9/2001 | Ponikau | |
| 6,382,205 B1 * | 5/2002 | Weinstein et al. | 128/200.23 |
| 6,416,955 B1 | 7/2002 | Sherris et al. | |
| 6,555,566 B2 | 4/2003 | Ponikau | |
| 6,919,348 B2 * | 7/2005 | Wei | 514/269 |
| 6,946,118 B1 | 9/2005 | Lawter et al. | |
| 2002/0169422 A1 | 11/2002 | Ahnblad et al. | |
| 2005/0226925 A1 * | 10/2005 | Singh | 424/464 |
| 2006/0051415 A1 | 3/2006 | Chow et al. | |
| 2006/0110333 A1 * | 5/2006 | Yanagawa | 424/46 |
| 2006/0147391 A1 | 7/2006 | Kim et al. | |
| 2006/0204448 A1 * | 9/2006 | Matsuyama et al. | 424/46 |
| 2008/0008753 A1 | 1/2008 | Singh | |
| 2008/0131420 A1 | 6/2008 | O'Donnell | |
| 2009/0258000 A1 | 10/2009 | O'Donnell et al. | |
| 2011/0104166 A1 | 5/2011 | Stankovic et al. | |

FOREIGN PATENT DOCUMENTS

| | | |
|---|---|---|
| WO | WO 98/11866 A1 | 3/1998 |
| WO | WO 2008/008494 A3 | 1/2008 |
| WO | WO 2008/063756 A3 | 5/2008 |

OTHER PUBLICATIONS

Amphotericin B Suspension in Refractory Chronic Sinusitis, ClinicalTrials.gov Identifier: NCT00425620, first received on Jan. 19, 2007, pp. 1-3, retrieved from http://clinicaltrials.gov/ct2/show/NCT00425620?term=amphotericin+and+lavage&rank=1 on Dec. 6, 2011.

Accentia Biopharmaceuticals Announces Results on Primary Endpoint in Clinical Study of SinuNase Lavage, released Mar. 24, 2008, pp. 1-2, retrieved from http://markets.financialcontent.com/ir/?Module=MediaViewer&GUID=4980592&Ticker=ABPI on Dec. 6, 2011.

Atlas, S.J. et al. "Validity of a New Health-Related Quality of Life Instrument for Patients with Chronic Sinusitis" *The Laryngoscope*, 2005, pp. 846-854, vol. 115.

Atlas, S.J. et al. "Development and validation of a new health-related quality of life instrument for patients with sinusitis" *Quality of Life Research*, 2005, pp. 1375-1386, vol. 14.

(Continued)

*Primary Examiner* — Mina Haghighatian

(74) *Attorney, Agent, or Firm* — Saliwanchik, Lloyd & Eisenschenk

(57) ABSTRACT

The present invention is directed to compositions, devices, and methods for non-irritatively treating and preventing mucositis, such as chronic rhinosinusitis (CRS). Some aspects of the invention concern compositions comprising or consisting essentially of sodium phosphate buffer (e.g., sodium phosphate dibasic and sodium phosphate monobasic) and calcium carbonate; mucoadministration devices and kits containing such compositions; and methods for treating or preventing mucositis conditions such as CRS, comprising mucoadministering a composition of the invention to a subject in need thereof.

19 Claims, 5 Drawing Sheets

(56) References Cited

OTHER PUBLICATIONS

Liang, K-L. et al. "Amphotericin B irrigation for the treatment of chronic rhinosinusitis without nasal polyps: A randomized, placebo-controlled, double-blind study" *Am J Rhinol*, 2008, pp. 52-58, vol. 22.

International Search Report dated Oct. 29, 2009 for PCT/US2009/039317, filed Apr. 2, 2009.

Pondrom, S. "Fungal Theory Debated in Amphotericin B Controversy" *ENToday*, Mar. 2008, pp. 12-13, vol. 3.

Rank, M.A. et al. "Antifungal therapy for chronic rhinosinusitis: the controversy persists" *Current Opinion in Allergy and Clinical Immunology*, 2009, pp. 67-72, vol. 9.

Scheid, D.C. et al. "Acute Bacterial Rhinosinusitis in Adults: Part II. Treatment" *Am Fam Physician*, Nov. 2004, pp. 1697-1704, vol. 70, No. 9.

Shin, S-H. et al. "Chronic rinosinusitis: An enhanced immune response to ubiquitous airborne fungi" *J Allergy Clin Immunol*, 2004, pp. 1369-1375, vol. 114.

SinuNase™ Fast-Tracked Pivotal Phase 3 Study in Chronic Sinusitis Shows Statistically Significant Objective Evidence of Superiority of SinuNase Over Control Lavage in Severe Cases, released Apr. 30, 2008, pp. 1-2, retrieved from http://markets.financialcontent.com/ir/?Module=MediaViewer&GUID=5334446&Ticker=ABPI on Dec. 6, 2011.

Stankiewicz, J.A. et al. "Nasal amphotericin irrigation in chronic rhinosinusitis" *Current Opinion in Otolaryngology & Head and Neck Surgery*, 2008, pp. 44-46, vol. 16.

Verdi, C.J. et al. "A double-blind, randomized, placebo-controlled, crossover trial of pentoxifylline for the prevention of chemotheraphy-induced oral mucositis" *Oral Surg, Oral Med, Oral Pathol, Oral radiol Endod*, 1995, pp. 36-42, vol. 80.

Wallace, D.V. et al. "The Diagnosis and Management of Rhinitis: An Updated Practice Parameter" *Journal of Allergy and Clinical Immunology*, Aug. 2008, pp. S1-S84, vol. 122, No. 2, Suppl. 1.

\* cited by examiner

Figure 1A

Rhinosinusitis Quality of Life Survey

YOUR RECENT SINUS / NASAL SYMPTOMS

- Answer questions by checking the box to the left of your answer.

- Please be sure to carefully answer every question. Do not skip any questions.

1. In the last 7 days, how much of the time did you have sinus headaches, facial pain or facial pressure?

☐ None of the time
    ☐ A little of the time
    ☐ Some of the time
    ☐ Most of the time
    ☐ All of the time 1a. Using a scale of 0 to 10, where 0 is not bothered at all and 10 is bothered a lot, how much were you bothered by the sinus headaches, facial pain or facial pressure?

☐ ☐ ☐ ☐ ☐ ☐ ☐ ☐ ☐ ☐ ☐

0  1  2  3  4  5  6  7  8  9  10
    Not                    Bothered
    Bothered                A Lot
    at All 2. In the last 7 days, how much of the time did you have a blocked or stuffy nose?

☐ None of the time
    ☐ A little of the time
    ☐ Some of the time
    ☐ Most of the time
    ☐ All of the time

Figure 1B

2a. Using a scale of 0 to 10, where 0 is not bothered at all and 10 is bothered a lot, how much were you bothered by having a blocked or stuffy nose?

☐ ☐ ☐ ☐ ☐ ☐ ☐ ☐ ☐ ☐ ☐

0   1   2   3   4   5   6   7   8   9   10
Not                    Bothered
Bothered            A Lot
at All 3. In the last 7 days, how much of the time did you have postnasal drip?

☐ None of the time
☐ A little of the time
☐ Some of the time
☐ Most of the time
☐ All of the time 3a. Using a scale of 0 to 10, where 0 is not bothered at all and 10 is bothered a lot, how much were you bothered by this postnasal drip?

☐ ☐ ☐ ☐ ☐ ☐ ☐ ☐ ☐ ☐ ☐

0   1   2   3   4   5   6   7   8   9   10
Not                    Bothered
Bothered            A Lot
at All 4. In the last 7 days, how much of the time did you have a thick nasal discharge?

☐ None of the time
☐ A little of the time
☐ Some of the time
☐ Most of the time
☐ All of the time 5. In the last 7 days, how much of the time did you have a runny nose?

Figure 1C

- ☐ None of the time
- ☐ A little of the time
- ☐ Some of the time
- ☐ Most of the time
- ☐ All of the time 6. For these next questions, please think about *all* the nasal symptoms you've recently experienced.

In the last 7 days, how much of the time did you feel tired or fatigued *because of your nasal symptoms?*

- ☐ None of the time
   - ☐ A little of the time
   - ☐ Some of the time
   - ☐ Most of the time
   - ☐ All of the time 7. In the last 7 days, how much of the time did you have trouble sleeping *because of your nasal symptoms?*

- ☐ None of the time
   - ☐ A little of the time
   - ☐ Some of the time
   - ☐ Most of the time
   - ☐ All of the time 8. In the last 7 days, how much of the time did you feel it was harder to concentrate *because of your nasal symptoms?*

- ☐ None of the time
   - ☐ A little of the time
   - ☐ Some of the time
   - ☐ Most of the time
   - ☐ All of the time

Figure 1D

9. In the last 7 days, how much of the time did you feel it was harder to do the things you normally do *because of your nasal symptoms*?

☐ None of the time
    ☐ A little of the time
    ☐ Some of the time
    ☐ Most of the time
    ☐ All of the time 10. In the last 7 days, how much of the time did you feel embarrassed *because of your nasal symptoms*?

☐ None of the time
    ☐ A little of the time
    ☐ Some of the time
    ☐ Most of the time
    ☐ All of the time 11. In the last 7 days, how much of the time did you feel frustrated *because of your nasal symptoms*?

☐ None of the time
    ☐ A little of the time
    ☐ Some of the time
    ☐ Most of the time
    ☐ All of the time 12. In the last 7 days, how much of the time did you feel irritable *because of your nasal symptoms*?

☐ None of the time
    ☐ A little of the time
    ☐ Some of the time
    ☐ Most of the time
    ☐ All of the time 13. In the last 7 days how much of the time did you feel sad or depressed *because of your nasal symptoms*?

Figure 1E

- ☐ None of the time
- ☐ A little of the time
- ☐ Some of the time
- ☐ Most of the time
- ☐ All of the time 14. In the last 7 days, how much of the time did you think about your nasal symptoms?

- ☐ None of the time
- ☐ A little of the time
- ☐ Some of the time
- ☐ Most of the time
- ☐ All of the time

THANK YOU FOR TAKING THE TIME TO COMPLETE THIS SURVEY!

US 8,940,319 B2

FORMULATIONS, DEVICES AND METHODS FOR TREATING AND PREVENTING MUCOSITIS

CROSS-REFERENCE TO RELATED APPLICATION

The present application is a continuation of U.S. patent application Ser. No. 12/534,575, filed Aug. 3, 2009, which is a continuation of U.S. patent application Ser. No. 12/417,378, filed on Apr. 2, 2009, which claims the benefit of U.S. Application Ser. No. 61/041,866, filed Apr. 2, 2008. Each of these applications is hereby incorporated by reference herein in its entirety, including any figures, tables, and drawings.

BACKGROUND OF THE INVENTION

Mucositis, the inflammation of mucosal tissue, is a serious medical problem that affects millions of people worldwide. In the respiratory tract, mucositis affects not only the nose, sinuses and the large airways but also the small airways of the lungs. Mucositis of the nasal cavity and/or paranasal sinuses is called rhinosinusitis. Rhinosinusitis is estimated to affect approximately 35 million Americans annually, and an estimated 90% of all rhinosinusitis cases are chronic (CRS). Of CRS sufferers, up to 500,000 people resort to sinus surgery each year.

CRS has been a confusing disease for medical providers due to a limited understanding of its pathophysiology and its limited treatment options. Due to the small number of controlled studies examining medical treatments for CRS, there are currently no FDA-approved medical treatments. The lack of robust clinical and laboratory markers to assess the severity of CRS has further hampered efforts to evaluate the efficacy of treatment.

CRS results in a variety of symptoms, including nasal congestion, facial pain and pressure, nasal discharge, and headaches. Historically, the treatment of CRS has largely focused on addressing the symptoms of the condition through acute antibiotic therapy, intranasal or oral corticosteroids, and sinus surgery. While antibiotics are useful in treating the acute exacerbations that result from the bacterial invasion of the damaged paranasal tissue of CRS patients, no antibiotic has proven effective in eradicating the underlying cause of CRS. Intranasal and oral corticosteroids, which are potent anti-inflammatory hormones, have been used to reduce the inflammation that plays a role in CRS, but oral corticosteroids can cause serious side effects and must be avoided or cautiously used with patients that have certain conditions, such as gastrointestinal ulcers, renal disease, hypertension, diabetes, osteoporosis, thyroid disorders, and intestinal disease. Surgery is frequently used in CRS patients to improve the drainage of their sinuses based on the assumption that the disease can be reversed by identifying and correcting the obstruction that caused the condition, but while such surgery usually offers temporary relief of symptoms, it is typically not curative.

Efforts to establish treatments for CRS have been frustrated by the reported heterogeneity of the disease. A variety of causes have been suggested for CRS, including bacterial infection, viral infection, fungal allergy (allergic fungal sinusitis), fungal infection (invasive), ubiquitous fungi leading to an inappropriate immune response, humoral immunodeficiency, and allergic and nonallergic rhinitis. Several studies have contributed to the accumulating body of literature that examines the efficacy of antifungal treatments of CRS. Research into the pathophysiology of CRS led to the discovery that eosinophils appear to become activated in the presence of fungi, and that fungi were ubiquitous in nasal secretions in both CRS patients and healthy individuals (Ponikau J. U. et al., "The diagnosis and incidence of allergic funal sinusitis," *Mayo Clin. Proc.*, 74:877-884 (1999)). Furthermore, an aberrant Th2-like immune response to fungi was observed in peripheral blood mononuclear cells from patients with CRS compared to controls (Shin S. H. et al., "Chronic rhinosinusitis: an enhanced immune response ubiquitous airborne fungi," *J. Allergy Clin. Immunol.*, 114:369-1375 (2004)). This research formed the basis for the fungi-immunological response hypothesis, which remains controversial today, i.e., that elimination of fungi will attenuate the aberrant immune response involving IL-5 production, eosinophil accumulation and activation, and toxic effects from release of eosinophil mediators such as eosinophilic major basic protein (Rank, M. A. et al., "Antifungal therapy for chronic rhinosinusitis: the controversy persists," *Curr. Opin. Allergy Clin. Immunol.*, 9:67-72 (2009)). U.S. Pat. Nos. 6,555,566, 6,291,500 and 6,207,703, by Dr. Jens Ponikau and assigned to the Mayo Foundation For Medical Education And Research, describe and claim methods of treating non-invasive fungus-induced rhinosinusitis, asthma, or intestinal mucositis by directly mucoadministering to at least a portion of the nasal-paranasal anatomy of the subject a formulation including an antifungal agent in an amount, at a frequency, and for a duration effective to reduce or eliminate the non-invasive fungus-induced rhinosinusitis, asthma, or intestinal mucositis. The contents of these references are incorporated in their entireties by this reference.

Mucositis is also a dose-limiting side effect of cancer therapy and bone marrow transplantation (Sonis, "Oral Complications," in: Cancer Medicine, pp. 2381-2388, Holand et al.; Eds., Lea and Febiger, Philadelphia (1993a); Sonis, "Oral Complications in Cancer Therapy," In: Principles and Practice of Oncology, pp. 2385-2394, De Vitta et al., Eds., J. B. Lippincott, Philadelphia (1993b). Oral mucositis is found in almost 100% of patients receiving radiotherapy for head and neck tumors, in about 40% of patients receiving chemotherapy, and in about 90% of children with leukemia (Sonis, 1993b, supra). Complications related to oral mucositis, though varying in the different patient populations, generally include pain, poor oral intake with consequent dehydration and weight loss, and systemic infection with organisms originating in the oral cavity leading to septicemia (Sonis, 1993b; U.S. Pat. No. 6,025,326, by Steinberg et al., assigned to IntraBiotics Pharmaceuticals, Inc.; U.S. Pat. No. 6,946,118, by Lawter et al., assigned to Orapharma, Inc.), In addition to the oral cavity, mucositis may also affect other parts of the gastrointestinal tract. Various approaches to treating oral mucositis and associated oral infections have been investigated with limited success (Loprinzi et al., *Sem. Oncol.* 22 Suppl. 3): 95-97 (1995); Epstein & Wong, *Int. J. Radiation Oncology Biol. Phys.* 28:693-698 (1994); Verdi et al., *Oral Surg. Oral Med. Oral Pathol. Oral Radiol. Endod.* 80:36-42 (1995)).

Despite the clear need for effective agents to treat and prevent mucositis, none of the current interventions provide significant long-term relief or significantly decrease the severity or duration of mucositis, particularly CRS. There is currently no curative treatment for mucositis.

BRIEF SUMMARY OF THE INVENTION

The present invention pertains to a mucosally non-irritative composition useful for treating or preventing mucositis, such as chronic rhinosinusitis (CRS). The present invention provides compositions comprising or consisting essentially of sodium phosphate buffer and calcium carbonate that are useful for treating or preventing mucositis; delivery devices (mucoadministration devices) containing compositions for mucoadministration of the compositions; methods for treating or preventing mucositis in a subject, comprising mucoadministering a composition of the invention to the subject; and kits for treating or preventing mucositis.

Preferably, the composition is mucoadministered to the subject using a mucoadministration device, such as a nasal irrigation device (nasal irrigator, such as a syringe with a flexible elastomeric outlet portion), pump spray device (nasal pump sprayer), or nebulizer. The composition of the invention comprises sodium phosphate buffer and calcium carbonate. Preferably, the composition comprises sodium phosphate dibasic, sodium phosphate monobasic, and calcium carbonate. In some embodiments, the composition consists essentially of the sodium phosphate buffer (e.g., sodium phosphate dibasic and sodium phosphate monobasic) and calcium carbonate.

In some embodiments, the present invention provides a method of treating a subject having mucositis. The method generally includes mucoadministering a composition as described herein at or proximal to the site of mucositis in the subject suffering from mucositis. In some embodiments, the composition is administered in an amount, at a frequency, and for a duration effective to reduce or eliminate the mucositis.

Optionally, the methods of the invention further comprise verifying that the subject is suffering from a form of mucositis, such as chronic rhino sinusitis or other form of mucositis, prior to mucoadministration of the composition.

In some embodiments, the present invention provides a method for preventing mucositis (e.g., completely avoiding or delaying onset of mucositis) in a subject. The method generally includes mucoadministering a composition as described herein to a subject that is not suffering from mucositis, or at least not suffering from mucositis at the anatomical site(s) where the composition is mucoadministered. In some embodiments, the subject is one identified as being at risk for developing mucositis.

BRIEF DESCRIPTION OF THE DRAWINGS

FIGS. 1A-1E are questions of the Rhinosinusitis Quality of Life Survey used in the clinical study described in Example 1.

DETAILED DESCRIPTION OF THE INVENTION

The present invention is directed to methods and compositions for treating and preventing mucositis, such as chronic rhinosinusitis (CRS). Specifically, the present invention provides: a mucosally non-irritative composition comprising or consisting essentially of sodium phosphate buffer (such as sodium phosphate dibasic and sodium phosphate monobasic) and calcium carbonate; methods for treating and preventing mucositis comprising mucoadministering an effective amount of the composition of the invention to a subject in need thereof; mucoadministration devices (such as a silicone tipped syringe) containing the composition of the invention; and kits comprising the composition of the invention and one or more additional components selected from a mucoadministration device, a mixing chamber, a diluent, and/or printed instructions for carrying out one or more of the methods described herein.

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a sachet" includes one or more sachets, reference to "a mucoadministration device" includes one or more of such devices, reference to "a mixing chamber" includes one or more of such chambers, and the like.

As used herein, the term "free or essentially free of" any component refers to the presence of the component in an amount less than that which would render the component mucosally irritative. In some embodiments, the term "free or essentially free of" any component refers to less than about 3% of the component being present in a composition, e.g., a solid composition. In other embodiments, the term "free or essentially free of" any component refers to less than about 2% of the component being present in a composition, e.g., a solid composition. In other embodiments, the term "free or essentially free of" any component refers to less than about 1% of the component being present in a composition, e.g., a solid composition. In still other embodiments, the term "free or essentially free of" any component refers to less than about 0.5% of the component being present in a composition, e.g., a solid or liquid composition. In some embodiments, the term "free or essentially free of" any component refers to less than about 0.1% of the component being present in a composition, e.g., a liquid composition.

As used herein, the term "mucoadministration" refers to any type of administration that places an administered agent in contact with mucus. Mucoadministration can be carried out using a mucoadministration device such as a nasal pump sprayer, nasal irrigator, or nebulizer. For example, the mucoadministration device can be a nasal irrigator having an outlet portion adapted to seal a subject's nostril during mucoadministration, such as the nasal rinser described in U.S. Patent Application Publication US 2002/0169422 (Ahnbled and Lagerqvist, filed Jun. 4, 2002), which is incorporated herein by reference in its entirety. Preferably, the nasal irrigator has an outlet portion made of a flexible material, such as silicone. Other examples of mucoadministration devices that can contain and deliver the compositions of the invention include bulb syringes, graduated syringes, and water jet devices (e.g., a Waterpik type of jet irrigation device).

For the purpose of this invention, the term "mucositis" as used herein refers to inflammation of a mucus membrane, including acute and chronic mucositis. Examples of mucosal tissue include, without limitation, the mucosa of the mouth, gut, nasal passages, paranasal sinuses, airways of the lung, trachea, middle ear, eustachian tube, vagina, and urethra. Typical inflammations of the mucous membranes include, but are not limited to, chronic rhinosinusitis such as non-invasive fungus-induced rhinosinusitis, chronic otitis media, chronic colitis, and Crohn's disease and chronic asthma symptoms. The term chronic rhinosinusitis or CRS refers to inflammation of the mucosa of the nose and paranasal sinuses lasting 12 weeks or longer, including but not limited to inflammation caused by one or more causal factors selected from among bacterial infection, viral infection, fungal allergy (allergic fungal sinusitis), invasive fungal infection, ubiquitous fungi leading to an inappropriate immune response (non-invasive, fungus-induced rhinosinusitis), humoral immunodeficiency, and allergic and nonallergic rhinitis. Unless specified otherwise, the term "chronic" as used herein refers to afflictions present for at least three months. It is to be understood that afflictions that are treated as described herein and become asymptomatic can be classified as chronic. Thus, chronic afflictions can be symptomatic or asymptomatic. In general, an inflammation of a mucosal tissue (such as CRS) can be determined using methods known in the art. As used herein, the terms "non-irritative" and "non-irritatively" refer to compositions and methods which exhibit no or negligible burning, stinging, itching or otherwise uncomfortable sensations when mucoadministered. In some embodiments, non-irritative compositions and methods also exhibit no or negligible odor, taste or aftertaste.

The terms "subject," "patient," and "individual" are used interchangeably herein to refer to mammals of any gender or age, including, but not limited to, humans, primates, cows, sheep, goats, horses, pigs, dogs, cats, rabbits, guinea pigs, rats, mice or other bovine, ovine, equine, canine, feline, rodent or murine species.

"Treatment", or "treating" as used herein, is defined as the application or administration of a therapeutic agent to a subject who has a disorder, e.g., mucositis as described herein, with the purpose to cure, heal, alleviate, delay, relieve, alter, remedy, ameliorate, improve or affect the disease or disorder, or symptoms of the disease or disorder. The term "treatment" or "treating" is also used herein in the context of administering agents prophylactically, which includes complete prevention or avoidance of all symptoms of the disorder, as well as delay in onset of one or more symptoms (e.g., all symptoms) of the disorder. With respect to the compositions of the invention, the term "treatment" or "treating" involves mucoadministration of the composition. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a subject already suffering from the disorder.

As used herein, the term "universally," when used in reference to non-irritative compositions and methods, refers to instances where at least 90% of the subjects to which a composition is administered experience no or negligible burning, stinging, etc. In some embodiments, the term universally includes instances where at least 95% of the subjects experience no or negligible burning, stinging, etc. In other embodiments, the term universally includes instances where 100% of the subjects experience no or negligible burning, stinging, etc. Preferably, the compositions of the invention are universally non-irritative.

Numerous values and ranges are recited in connection with various embodiments of the present invention, e.g., amount of sodium phosphate buffer and calcium carbonate. It is to be understood that all values and ranges which fall between the values and ranges listed are intended to be encompassed by the present invention unless stated otherwise.

I. Compositions of the Invention

The present invention includes compositions comprising or consisting essentially of sodium phosphate buffer (such as sodium phosphate dibasic and sodium phosphate monobasic) and calcium carbonate. Preferably, the compositions and methods cause no or negligible burning when mucoadministered the subject. The composition is generally a mucosally non-irritative mixture of ingredients. Preferably, the composition is universally non-irritative. Accordingly, the present invention provides mucosally non-irritative compositions useful for treating or preventing mucositis.

In some embodiments, the composition comprises one or more doses effective in treating or preventing mucositis (e.g., CRS) in a human subject through mucoadministration.

Preferably, the composition comprises or consists essentially of sodium phosphate dibasic, sodium phosphate monobasic, and calcium carbonate. Optionally, the composition further includes water (e.g., sterile water, deionized water, or tap water). Optionally, the composition further comprises a dye, such as FD&C Yellow #5 (tetrazine).

In some embodiments, the sodium phosphate dibasic is present in an amount between about 45% and about 70% by weight of the total composition; and wherein the sodium phosphate monobasic is present in an amount between about 30% and about 55% by weight of the total composition.

In some embodiments, the composition comprises or consists essentially of about 2% to about 3% (w/w) sodium phosphate buffer and about 0.005 to about 0.030% (w/w) calcium carbonate. In some embodiments, the composition comprises or consists essentially of about 2.55% (w/w) sodium phosphate buffer and about 0.015% (w/w) calcium carbonate. In some embodiments, the composition comprises or consists essentially of 1.59% (w/w) sodium phosphate dibasic, 0.96% (w/w) sodium phosphate monobasic, and 0.015% (w/w) calcium carbonate. Table 1 is an embodiment of a composition of the invention.

TABLE 1

| Ingredient | % w/w |
| --- | --- |
| Sodium Phosphate Dibasic, Anhydrous, USP | 1.59 |
| Sodium Phosphate Monobasic, Anhydrous, USP | 0.96 |
| Calcium Carbonate, USP | 0.015 |
| Dye | 0.0015 |
| Sterile Water | QS |

In some embodiments, the composition is a powder to be reconstituted in a diluent such as water (e.g., sterile water, deionized water, or tap water) prior to mucoadministration. In other embodiments, the composition is a powder that can be mucoadministered in its powder form. In other embodiments, the composition is a liquid (e.g., a solution or suspension).

In some embodiments, e.g., where the composition is in solid form, the solid form is preferably suitable for incorporation into a solution or suspension. For example, in some embodiments, water (e.g., sterile water) is added to the composition of the present invention to form a solution or suspension. Such a solution or suspension would be suitable for non-irritative mucoadministration.

In some embodiments, the composition is in solid form (e.g., a powder) and mixed with a diluent, such as sterile water, to solution. Preferably, the solution is agitated (e.g., shaken) if necessary to dissolve any large particles (e.g., particles of sodium chloride or sodium phosphates). The solution can then be taken up by a mucoadministration device, such as a syringe, and mucoadministered to the target mucosa, such as the nasal and/or paranasal cavity.

Compositions of the present invention may include a pharmaceutically acceptable carrier or diluent. The pharmaceutically acceptable carrier can be a solid vehicle. Examples of pharmaceutically acceptable solid vehicles include, but are not limited to, gelatin, starch, sugar, or bentonite.

The composition can be buffered as necessary to provide a desired pH. Appropriate buffer systems include citrate, acetate, tromethamine and benzoate systems. However, any buffer system commonly used for preparing medicinal compositions would be appropriate. Thus, in some embodiments, the composition includes buffering agents. The term "buffering agent" refers to one or more components which are added to a composition in order to adjust or maintain the pH of the composition. Suitable buffering agents are known to the skilled artisan and include, but are not limited to phosphates, carbonates, borates, lactates, acetates, and citrates, and combinations thereof, particularly alkali metal or alkaline metal salts of these agents. It is to be understood that buffering agents useful for the present invention are non-irritative. In some embodiments, the buffering agents are sodium phosphate buffering agents.

pH adjusting substances in accordance with the present invention can be used to provide further mucosal permeation enhancement. The most preferred pH adjusting substance is a carbonate, bicarbonate, or phosphate. The pH is the "localized pH" at the microenvironment at the surface contact area of the target mucosa and the compositions of the invention or any portion thereof.

The pharmaceutically acceptable carrier can be an aqueous vehicle, e.g., any liquid solution capable of dissolving a solid form of the composition and is not toxic to the particular individual receiving the formulation. Examples of pharmaceutically acceptable aqueous vehicles include, but are not limited to, saline, water, and acetic acid. Typically, pharmaceutically acceptable aqueous vehicles are sterile. In some embodiments, the pharmaceutically acceptable carrier includes sterile water. It is to be understood that additional aqueous vehicles are also suitable for the compositions of the present invention, provided that they are non-irritative and not toxic.

Accordingly, in some embodiments, the composition is a liquid. For example, in some embodiments, the composition includes water, e.g., sterile water, deionized water, or tap water. In other embodiments, the composition includes saline. Typically, the saline or water used in compositions of the present invention is sterile. In some embodiments, compositions of the present invention include at least 96.50% by weight water. In some embodiments, compositions of the present invention include at least 96.75% by weight water. In some embodiments, compositions of the present invention include at least 97.00% by weight water. In some embodiments, compositions of the present invention include at least 97.25% by weight water. In some embodiments, e.g., where the composition is in liquid form, the sodium phosphate dibasic is present in an amount of about 1.59% by weight of the total composition. In some embodiments, e.g., where the composition is in liquid form, the sodium phosphate monobasic is present in an amount of amount of about 0.96% by weight of the total composition. In some embodiments, e.g., where the composition is in liquid form, water is present in an amount of amount of about 97.44% by weight of the total composition.

While the vehicle used generally is primarily water, other vehicles may be present such as alcohols, glycols (polyethylene glycol or polypropylene glycol are examples), glycerin, and the like may be used to solubilize the active agents. Surfactants may include anionic, nonionic, amphoteric and cationic surfactants, which are known in the art as appropriate ingredients for mouthwashes.

The composition of the invention can be in any form provided the composition can be non-irritatively mucoadministered to a subject in an amount, at a frequency, and for a duration effective to prevent, delay onset of, reduce, or eliminate a mucositis. For example, a composition within the scope of the invention can be in the form of a solid, liquid, and/or aerosol including, without limitation, powders, crystalline substances, gels, pastes, ointments, salves, creams, solutions, suspensions, lavages, partial liquids, sprays, nebulae, mists, atomized vapors, tinctures, pills, capsules, tablets, and gel caps.

The composition may include other conventional excipients in generally known amounts to the extent they do not detract from the advantages described herein. These can include without limitation binders, sweeteners, coloring components (dyes), flavors, glidants, lubricants, preservatives, fillers, noneffervescent disintegrants, and the like.

Liquid formulations of the composition may contain additional components to improve the effectiveness of the product. For example, component(s) may be added to increase viscosity to provide improved retention on the surfaces of the target site(s). Suitable viscosity increasing agents include carboxyalkyl, hydroxyalkyl, and hydroxyalkyl alkyl celluloses, xanthan gum, carageenan, alginates, pectins, guar gum, polyvinylpyrolidone, and gellan gums. High viscosity formulations may cause nausea in chemotherapy and radiation patients and are therefore not preferred in those applications. Gellan gums are preferred as viscosity modifying agents since aqueous solutions containing certain gellan gums may be prepared so that they will experience an increase in viscosity upon contact with electrolytes. Saliva contains electrolytes that will interact with such a gellan containing solution so as to increase their viscosity.

Flavorings used in the mouth rinse art such as peppermint, citrus flavorings, berry flavorings, vanilla, cinnamon, and sweeteners, either natural or artificial, may be used. Flavorings that are known to increase salivary electrolyte concentrations may be added to increase the magnitude of a viscosity change. The increased viscosity will promote retention of the solutions at the oral cavity, for example, and provide greater effectiveness due to increased contact time with the affected tissues.

In order to improve the patient acceptability, it may be desirable to add an appropriate coloring (dye) and/or flavoring material. Any pharmaceutically acceptable coloring or flavoring material may be used.

Additional antimicrobial preservatives may be components of the composition in cases where it is necessary to inhibit microbial growth. Suitable preservatives include, but are not limited to the alkyl parabens, benzoic acid, and benzyl alcohol. The quantity of preservative may be determined by conducting standard antimicrobial preservative effectiveness tests such as that described in the United States Pharmacopoeia.

Suitable solid dosage forms include powders or tablets that are designed for constitution as solutions by dissolution or suspension in a liquid vehicle and include troches, pastilles or lozenges, for example, which dissolve slowly in the mouth. For convenience of use, solids designed to be dissolved to prepare a liquid dosage form prior to mucoadministration preferably are rapidly dissolving. Technologies to produce rapidly dissolving solids are well known in the art. These include spray-drying, freeze-drying, particle size reduction and optimizing the pH of the dissolution medium.

Other medicinal agents may be included in the composition for purposes of alleviating other undesirable conditions in the subject at the target site and/or elsewhere. Such active agents may include, for example, local anesthetics, antibacterial agents, and emollients, as well as anti-fungal agents. Preferably, the composition of the invention includes no additional active agents.

Optionally, the composition includes one or more antifungal agents, steroids, mucolytic agents, antibacterial agents, anti-inflammatory agents, immunosuppressants, dilators, vaso-constrictors, decongestants, leukotriene inhibitors, anticholinergics, anti-histamines, additional therapeutic compounds, compounds known to be effective for inhibiting the gag reflex of a mammal, and combinations of two or more of the foregoing. Accordingly, in some embodiments, the composition of the invention contains none of the foregoing agents (e.g., no antifungal agents, such as amphotericin B).

Preferably, the composition of the present invention is free or essentially free of components that may be irritative to the mucosa, e.g., the nasal-paranasal mucosa. In some embodiments, the compositions of the present invention are free or essentially free of solvent, e.g., propylene glycol. In some embodiments, the compositions of the present invention are free or essentially free of antioxidants, e.g., sodium metabisulfate. In some embodiments, the compositions of the present invention are free or essentially free of a thickening or suspending agent, e.g., carboxymethylcellulose sodium. In still other embodiments, the compositions of the present invention are free or essentially free of antimicrobials, e.g., methylparaben and/or propylparaben. In yet other embodiments, the compositions of the present invention are free or essentially free of bile salts and/or emulsifiers, e.g., deoxycholate salts such as sodium deoxycholate. In some embodiments, compositions of the present invention are free or essentially free of combinations or mixtures of one or more solvents (e.g., propylene glycol), antioxidants (e.g., sodium metabisulfate), thickening or suspending agents (e.g., carboxymethylcellulose sodium), antimicrobials (e.g., methylparaben and/or propylparaben), bile salts and/or emulsifiers (e.g., deoxycholate salts).

In some embodiments, the compositions of the present invention further include one or more polysaccharide degrading enzymes. As used herein, the term "polysaccharide degrading enzyme" refers to an enzyme that cleaves glycosidic bonds. Without wishing to be bound by any particular theory, it is believed that such an enzyme would cleave the glycosidic bonds of polysaccharides present in mucus and, thereby aid in breaking up thick secretions, e.g., by reducing the viscosity of mucus. Examples of a polysaccharide degrading enzyme include, but are not limited to, β-glucosidase, pullulanase, neuraminidase and hyaluronidase. In a particular embodiment, the polysaccharide degrading enzyme is hyaluronidase. Accordingly, in some embodiments, the present invention provides for mucoadministration of the composition of the invention and a polysaccharide degrading enzyme, separately or within the same formulation.

II. Methods for Treatment or Prevention of Mucositis

The compositions of the present invention, which comprise or consist essentially of amounts of a sodium phosphate buffer (such as sodium phosphate dibasic and sodium phosphate monobasic) and calcium carbonate as components, can be mucoadministered to a subject at a frequency and for a duration effective to treat or prevent mucositis. Thus, another aspect of the present invention is directed to methods and compositions for treating and preventing mucositis comprising mucoadministering a composition of the invention to a subject in need thereof. In some embodiments, the subject is one suffering from mucositis and the composition is administered at or proximal to the site of mucositis. In other embodiments, the subject is one that is not suffering from mucositis but is at risk for developing mucositis. In some embodiments in which the subject is not suffering from mucositis, but is at risk for developing mucositis, the subject has previously suffered from mucositis. In some embodiments in which the subject is not suffering from mucositis, but is at risk for developing mucositis, the subject has been treated or will be treated with chemotherapy and/or radiation therapy.

An effective amount of a composition of the invention can be any amount that reduces, prevents, or eliminates mucositis upon mucoadministration in a subject without producing significant toxicity to the subject. Various factors can influence the actual effective amount used for a particular application. For example, the frequency of mucoadministration, duration of treatment, administration of other agents, site of administration, degree of inflammation, and the anatomical configuration of the target area may require an increase or decrease in the actual effective amount of composition mucoadministered.

In some embodiments, the subject is suffering from CRS, and mucoadministration of the composition results in a reduction of eosinophils in the subject, a reduction of eosinophilic major basic protein (eMBP) in the subject, or both. In some embodiments, the subject is suffering from CRS, and mucoadministration of the composition results in alleviation or resolution of one or signs or symptoms of CRS, such as congestion, sinus headache, polyposis, and mucosal thickening. In some embodiments, the subject is suffering from CRS, and mucoadministration of the composition results in a reduction of polyposis and/or sinus inflammation in the subject. In some embodiments, the subject is suffering from CRS, and mucoadministration of the composition results in improvement in one or more of the symptoms (e.g., headache, congestion, cough, facial pain) and/or scores (e.g., RhinoQOL, CSS, endoscopy, CT scan) listed in Table 3 or Table 4.

In some embodiments, mucoadministration is achieved via a lavage. In other embodiments, mucoadministration is achieved via a pump spray. Accordingly, in some embodiments, mucoadministration includes from 1 to 4 pumps per nostril, e.g., 3 pumps per nostril. In some embodiments, the pump dispenses between about 50 μL and about 200 μL of the composition, e.g, about 100 μL of the composition. In other embodiments, an effective amount is 20 mL per nostril of the composition per administration (e.g., two to four times daily) for nasal irrigation.

It is to be understood that the volume mucoadministered can be administered in one single event or in multiple events. For example, 20 mL per nostril of the composition can be administered as a continuous irrigation, wash (lavage) or spray of the entire 20 mL. Alternatively, administration can include two or more sequential applications of a portion of the exemplary 20 mL (e.g., 2 washes/sprays of 10 mL each, 4 washes/sprays of 5 mL each, etc.). It is also to be understood that, when a volume is administered via two or more sequential applications, each application need not be equivalent to the previous application. For example, 20 mL of the composition can be administered via 1 wash/spray of 10 mL followed by 2 washes/sprays of 5 mL each. In some embodiments, the composition is mucoadministered to all of a part of the nasal and/or paranasal anatomy in an amount between 0.1 mL to 1 L per nostril at a frequency of once, twice, three, or four times daily, and for a duration of two weeks to a human's life time (e.g., 30 days or more, 60 days or more, 90 days or more, etc.).

By way of a further example, a composition of the present invention can be administered by a pump from one to four times daily (e.g., three times daily). Each pump can have a volume of between about 50 μL and about 200 μL, e.g., a volume of about 100 μL. Furthermore, each single mucoadministration event can include from one to four pumps per nostril, e.g., three pumps per nostril.

The frequency of mucoadministration can be any frequency that reduces, prevents, or eliminates mucositis in a mammal without producing significant toxicity to the mammal. For example, the frequency of mucoadministration can be from about four times a day to about once a month, or more specifically, from about twice a day to about once a week. The frequency of mucoadministration can be four times a day, three times a day, two times a day, once a day, every other day, every third day, twice a week, once a week, once every two weeks, once every three weeks, or once a month. In addition, the frequency of mucoadministration can remain constant or can be variable during the duration of treatment. For example, the first three doses may occur within day one at a frequency of three times a day, but the next four doses may be administered at a frequency of twice a day, once a day, etc. As with the effective amount, various factors can influence the actual frequency of mucoadministration used for a particular application. For example, the effective amount, duration of treatment, combination of other agents, site of administration, degree of inflammation, and the anatomical configuration of the target area may require an increase or decrease in mucoadministration frequency.

An effective duration for mucoadministration can be any duration that reduces, prevents, or eliminates mucositis (e.g., CRS) in a mammal without producing significant toxicity to the mammal. Thus, the effective duration can vary from several days to several weeks, months, or years. In general, the effective duration for the treatment of mucositis can range in duration from several days to several months. Once the mucoadministrations are stopped, however, some cases of mucositis, such as CRS, may return. Thus, the effective duration for the prevention of mucositis can last in some cases for as long as the individual is alive. In some embodiments, an effective duration is at least 7 days. In other embodiments, an effective duration is at least 14 days. In still other embodiments, an effective duration is at least 30 days, 60 days, 90 days, 3 months, 6 months, 9 months, 1 year or more. Mucoadministration can be carried out by the subject (self-administration) or another, such as medical personnel.

Multiple factors can influence the actual effective duration used for a particular treatment or prevention regimen. For example, an effective duration can vary with the frequency of mucoadministration, effective amount, combination of the composition with other medicinal agents, site of administration, degree of inflammation, and anatomical configuration of the treated area. It is noted that diagnostic algorithm methods can be devised to determine or reflect appropriate effective doses, durations, and frequencies without any undue experimentation.

In some aspects, the present invention provides methods for treating CRS such as non-invasive fungus-induced mucositis. The method generally includes the mucoadministration of any of the compositions provided herein to a subject. Accordingly, in some embodiments, the non-irritative compositions of the present invention are suitable for administration to the mucosa (e.g., for mucoadministration to the nasal-paranasal cavities). In some embodiments, the composition of the present invention is administered in an amount, at a frequency, and for a duration effective to reduce or eliminate the CRS.

In general, most, if not all, individuals have fungal organisms living in their mucus. Normally, most individuals tolerate these non-invasive organisms and live normal disease-free lives. According to the fungi-immunological response hypothesis, some individuals do not tolerate these fungal organisms and begin to mount an immune response against them. As the immune response progresses, eosinophils accumulate within the local tissue. This accumulation of eosinophils can contribute to the formation of obstructive tissue masses (e.g., polyps and polypoid structures) as well as the transmigration of activated eosinophils from the tissue (inside the body) to the mucus (outside the body). These obstructive tissue masses appear to prevent normal cavity clearance and thus can facilitate additional fungal growth. Once eosinophils are within the mucus, they can release the contents of their granules presumably upon the activation of surface Fc receptors. Eosinophil granules contain many toxic molecules such as eosinophil cationic protein (ECP), eosinophil peroxidase (EPO), and major basic protein (MBP). Upon release, these toxic molecules can damage both the targeted foreign microorganisms (e.g., fungus) as well as self tissues. The degree of damage caused by eosinophil accumulation and eosinophil degranulation varies significantly from slight inflammatory pain and discomfort to major structural abnormalities such as tissue and bone destruction and the formation of polyps, polypoid structures, and other tumors. Once self tissues are damaged, the individual can have an increased susceptibility to bacterial infections as well. Thus, the fungi-immunological response hypothesis dictates that the characteristic inflammatory responses, resulting damages, and resulting bacterial infections observed within most, if not all, chronic rhinosinusitis patients are actually triggered by non-invasive fungal organisms. In some aspects, the present invention provides methods and compositions to reduce the amount of eosinophil and/or MBP in the mucosa of a subject by mucoadministration of a composition of the invention. The methods and compositions can be any of those described herein.

It is noted that fungal organisms may be observed within the tissue under extreme mucositis conditions of tissue and bone destruction simply because the barrier (i.e., epithelium) between the inside and outside of the body has been destroyed or damaged. In these situations, the mere observed presence of a small number of fungal organisms within a localized area of tissue damage does not deter from the fact that the affliction can be considered a non-invasive fungus-induced mucositis and not an infection.

Any fungal organism living in the mucus of a mammal can be a non-invasive fungal organism that is capable of inducing mucositis since, according to the hypothesis, it is the mere presence of the organism in an intolerant individual's mucus that causes inflammation. Exemplary fungal organisms include, but are not limited to, *Absidia, Aspergillus flavus, Aspergillus fumigatus, Aspergillus glaucus, Aspergillus nidulans, Aspergillus versicolor, Alternaria, Basidiobolus, Bipolaris, Candida albicans, Candida lypolytica, Candida parapsilosis, Cladosporium, Conidiobolus, Cunninahamelk Curvularia, Dreschlera, Exserohilum, Fusarium, Malbranchia, Paecilomvces, Penicillium, Pseudallescheria, Rhizopus, Schizophylum, Sporothrix, Acremonium, Arachniotus citrinus, Aurobasidioum, Beauveria, Chaetomium, Chrysosporium, Epicoccum, Exophilia jeanselmei, Geotrichum, Oidiodendron, Phoma, Pithomyces, Rhinocladiella, Rhodoturula, Sagrahamala, Scolebasidium, Scopulariopsis, Ustilago, Trichoderma*, and *Zygomycete*. Additional fungal organisms that can be non-invasive fungal organisms capable of inducing a non-invasive fungus-induced mucositis can be found in most taxonomic mycology text books.

Accordingly, some aspects of the present invention provide non-irritative methods and compositions that can reduce the presence of fungal organisms within mucus to a level and for a period of time such that the characteristic inflammatory responses and resulting damages associated with mucositis are stopped, treated, or prevented.

Mucoadministration for treatment or prevention of mucositis can be carried out using a mucoadministration device such as a nasal pump sprayer, nasal irrigator, or nebulizer. For example, the mucoadministration device can be a nasal irrigator having an outlet portion adapted to seal a subject's nostril during mucoadministration, such as the nasal rinser described in U.S. Patent Application Publication US 2002/0169422 (Ahnbled and Lagerqvist, filed Jun. 4, 2002), which is incorporated herein by reference in its entirety. Preferably, the nasal irrigator has an outlet portion made of a flexible elastomeric material, such as silicone. Other examples of mucoadministration devices that can contain and deliver the compositions of the invention include bulb syringes, graduated syringes, and water jet devices (e.g., a WATERPIK type of jet irrigation device).

Mucosa from any mucosal tissue can be treated with the compositions of the present invention. Examples of mucosal tissue include, but are not limited to, the mucosa of the mouth, gut, nasal passages, paranasal sinuses, airways of the lung, trachea, middle ear, eustachian tube, vagina, and urethra. In certain embodiments, the mucosa treated in the present invention is from the nasal passages and/or paranasal sinuses.

In some embodiments, the present invention provides methods for non-irritatively mucoadministering any of the compositions described herein to the nasal-paranasal cavities. Mucosal tissue (mucosa) lines both the nasal cavity and the paranasal sinuses, and generally comprises an epithelial layer, connective tissue, and mucus glands. A layer of mucus normally covers the mucosa. Mucus secreted from mucosa serves to trap particles and to prevent dehydration of the nasal and paranasal tissues that are otherwise exposed to air. The mucus is normally transported by cilia toward the nasopharynx and then swallowed.

The mucoadministration of the composition of the invention, e.g., to the nasal-paranasal anatomies, can be any type of administration that places the composition in contact with mucus, e.g., direct or indirect mucoadministration. In some embodiments, the mucoadministration of a composition of the present invention is direct mucoadministration. Direct mucoadministration to the nasal-paranasal anatomies can include, without limitation, nasal irrigations, nasal sprays, nasal inhalations, and nasal packs with, for example, saturated gauze provided the administered agent contacts nasal-paranasal mucus prior to crossing epithelium. In addition, injections into the nasal-paranasal cavities using, for example, a needle or catheter tube is considered a direct mucoadministration provided the administered composition contacts nasal-paranasal mucus after leaving the needle or catheter tube and prior to crossing epithelium. Any device can be used to directly mucoadminister the composition to the nasal-paranasal anatomy including, without limitation, a syringe, bulb, inhaler, canister, spray can, nebulizer, and mask. For example, a 20 mL bulb can be used to irrigate the nasal-paranasal anatomy with a liquid form of the composition. Such a liquid form of a formulation can be stored at −20° C., 0° C., or room temperature. If stored below room temperature, the formulation typically is warmed prior to application to the nasal/paranasal cavities.

In some embodiments, the subject had a nasal surgery before said mucoadministration. In other embodiments, the subject was nasal surgery-free before said mucoadministration. The compositions and methods of the present invention are useful for both subjects who have undergone nasal surgery as well as subjects who have never had nasal surgery. In some embodiments, mucoadministration begins during a period noncoincident with an intraoperative period, said intraoperative period being the time during a nasal surgery.

The compositions of the present invention are useful for the treatment of any mucositis. Typically, such conditions generally involve inflammations of the mucous membranes which include, but are not limited to, chronic rhinosinusitis, chronic non-invasive fungus-induced rhinosinusitis, chronic otitis media, chronic colitis, and Crohn's disease and chronic asthma symptoms.

In some embodiments, the present invention provides methods for treating non-invasive fungus-induced rhinosinusitis. Individuals suffering from rhinosinusitis can be identified using methods commonly known in the art. Symptoms of rhinosinusitis include, without limitation, nasal airway obstruction, loss of smell, facial pain, head ache, post nasal drip, and rhinorrhea. Upon examination, the presence of thick mucus or the visual identification of nasal or paranasal obstruction with mucus or polyps often indicates a rhinosinusitis condition. The presence of nasal polyps is not a risk factor for rhinosinusitis, but rather an end stage of chronic inflammation. Nasal polyps are outgrowths from the nasal-paranasal mucosa that are typically smooth, gelatinous, semi-translucent, round or pear shaped, and pale. The mass of a nasal polyp is composed mainly of edematous fluid with sparse fibrous cells and a few mucous glands. The surface epithelium of nasal and paranasal polyps generally reveals squamous metaplasia. Eosinophils are usually present in polyps in moderate to large numbers, and it is now known that nasal polyp fluid contains greater than normal concentrations of IgA, IgE, IgG, and IgM antibodies as well as abnormally high concentrations of IL-5, a cytokine that contributes to eosinophil activation and survival.

Any individual that had a previous episode of rhinosinusitis is at risk for developing CRS. In addition, elderly individuals as well as individuals having cystic fibrosis, asthma, and a family history of nasal problems or allergies can be at risk for developing CRS. Further, individuals that are exposed to significant levels of allergens (e.g., fungus spores, pollen, and chemicals) can be at risk for developing CRS. Accordingly, in some embodiments, the present invention provides compositions and methods for non-irritatively treating a subject at risk for developing CRS.

Other treatments can be used in combination with a composition of the invention to help enhance the treatment or prevention of chronic rhinosinusitis conditions. Such additional treatments can include, without limitation, surgeries and the administration of a second formulation. Surgeries can include, without limitation, the removal of polypoid growths or other tumors, the physical opening of a cavity, and the insertion of catheter tubes and the like. A second formulation can include, without limitation, antifungal agents, mucolytic agents, antibacterial agents, anti-inflammatory agents, immunosuppressants, dilators, vaso-constrictors, decongestants, steroids, anti-cholinergics, leukotriene inhibitors, anti-histamines, therapeutic compounds, and combinations thereof. In addition, this second formulation can be administered to a subject by any route. For example, oral, intraperitoneal, intradermal, intravenous, subcutaneous, intramuscular, topical, intranasal, and intrabronchial administration can be used to deliver a second formulation to a subject. In some embodiments, no additional treatment for mucositis is used in combination with the composition of the invention, i.e., the composition may used as a monotherapy.

Optionally, the methods of the invention further comprise verifying that the subject is suffering from a form of mucositis, such as chronic rhinosinusitis or other form of mucositis, prior to mucoadministration of the composition. For example, U.S. Pat. No. 6,416,955 (by Sherris et al., assigned to Mayo Foundation for Medical Education and Research, the entire contents of which are incorporated herein by reference) describes examining a sample of nasal and/or paranasal mucus to determine the presence or absence of a concentration of major basic protein.

Optionally, the method of the invention may further include additional steps aimed at determining the efficacy of the treatment. For example, in the case of CRS, the method may further include determining whether the subject experiences a decrease in sinus mucosal thickening in response to the treatment, experiences polypoid change in response to the treatment, and/or has a decrease in eMBP in the nasal or paranasal mucus in response to the treatment. Methods for determining polypoid improvement are known in the art (see, for example, Rasp G, Kramer M F, Ostertag P, Kastenbauer E. "A new system for the classification of ethmoid polyposis. Effect of combined local and systemic steroid therapy", *Laryngorhinootologie*, 79:266-72 (2000). In some embodiments, the methods of the invention include one or more of the following: determining whether the subject experiences a decrease in mucosal thickening and/or polypoid change in the turbinate in response to the treatment; determining whether the subject experiences a decrease in mucosal thickening in the maxillary sinus of the subject in response to the treatment; and determining the presence or absence of a concentration of eMBP within the nasal or paranasal mucus of the subject.

In some embodiments, the present invention also provides a method for treating and preventing asthma by mucoadministration of compositions as described herein. Asthma can be characterized by a paradoxical narrowing of the bronchi (lung passageways) such that breathing becomes difficult. Individuals suffering from asthma can exhibit symptoms such as wheezing, difficulty breathing (particularly exhaling air), dyspnea, and tightness in the chest. Factors that can exacerbate asthma include rapid changes in temperature or humidity, allergies, upper respiratory infections, exercise, stress, and smoking. Individuals suffering from asthma can be identified using any of the known methods in the art.

It is expected that the asthma patient will have no or few episodes of shortness of breath and no wheezing during the treatment period. Additionally, it is expected that the asthma patient will exhibit improved pulmonary function, improved forced vital capacity (FVC) of the lung, an increased forced expiratory volume in 1 second (FEV1), improved maximal forced expiratory flow (FEFmax), and/or improved maximum voluntary ventilation (MVV). It is expected that the results will demonstrate that chronic asthma symptoms can be treated and prevented by mucoadministering the compositions of the present invention to the airways.

Further, individuals at risk for developing chronic asthma can be prophylactically treated by mucoadministering the composition to at least a portion of the airways in an amount, at a frequency, and for a duration effective to prevent asthma symptoms. Again, such prophylactic treatments can be similar to the methods and materials described herein for the prophylactic treatment of CRS.

III. Devices for Delivery to Mucosa (Mucoadministration Devices)

Another aspect of the invention concerns mucoadministration devices containing a composition described herein. The term "mucoadministration device" refers to any delivery device designed for delivery of a substance to a mucosal surface. The devices are useful for storage and mucoadministration of the compositions of the invention. In some embodiments, the mucoadministration devices are sealed for storage of the composition, in solid, liquid, or semi-solid form, and may be packaged for distribution. The mucoadministration device can be, for example, a nasal pump sprayer, nasal irrigator (also known as a nasal irrigation device, such as a syringe), nebulizer, nasal inhaler or other nasal delivery device, or an oral inhaler. The mucoadministration device can be a nasal irrigator having an outlet portion adapted to seal a subject's nostril during mucoadministration, such as the nasal rinser described in U.S. Patent Application Publication US 2002/0169422 (by Ahnbled and Lagerqvist, filed Jun. 4, 2002), which is incorporated herein by reference in its entirety. Preferably, the nasal irrigator has an outlet portion made of a flexible material. More preferably, the flexible material is an elastomer, such as silicone. Other examples of mucoadministration devices that can contain and deliver the compositions of the invention include bulb syringes, graduated syringes, and water jet devices (e.g., a WATERPIK type of jet irrigation device).

Typically, mucoadministration devices have one or more channels, reservoirs, or other chambers for holding a volume of liquid for ejection and delivery to the mucosa, or are in fluid communication (such as by a tube) with another component having such a chamber. In this case, the chamber holds the composition of the invention. Typically, the devices will have an outlet end for the liquid to leave the device. Depending upon the mode of mucoadministration, the outlet end can be adapted to make contact with the body (such as the mouth, nostril, or other body orifice) and deliver the composition to the mucosa (e.g., a nasal irrigator, nasal pulsatile irrigator, or inhaler), or adapted to dispense the composition in close proximity to the mucosa (e.g., a dropper).

The mucoadministration device may have a plunger, piston, or other actuator for exerting a force on the composition sufficient to expel the composition out of the device (to the mucosa).

Typically, nasal irrigators (such as the Nasaline nasal irrigator or Emcur nasal douche) have a chamber within the device for holding a volume of liquid (e.g., 1-12 ounces). The chamber and/or outlet may be shaped to produce a stream (e.g., a swirly stream) or spray as it leaves the device. The tip or outlet of the device may partially or completely seal the nostril opening. In some embodiments, the mucoadministration device contains about 40 mL to about 60 mL of the composition in liquid form.

In some embodiments, the mucoadministration device contains the composition of the invention in powder form. The composition can be mucoadministered as a solid (e.g., powder), or a diluent such as water can be added to the composition in the device to make a solution or suspension prior to mucoadministration.

In some embodiments, the mucoadministration device is one which delivers the composition as an aerosol, metered aerosol, powder aerosol, spray aerosol, spray, metered spray, or suspension spray.

As used herein, the term "aerosol" refers to a product that is packaged under pressure and contains therapeutically active ingredients that are released upon activation of an appropriate valve system. As used herein, the term "metered aerosol" refers to a pressurized dosage form comprised of metered dose valves, which allow for the delivery of a uniform quantity of spray upon each activation. As used herein, the term "powder aerosol" refers to a product that is packaged under pressure and contains therapeutically active ingredients in the form of a powder, which are released upon activation of an appropriate valve system. As used herein, the term "spray aerosol" is an aerosol product that utilizes a compressed gas as the propellant to provide the force necessary to expel the product as a wet spray; it generally applicable to solutions of medicinal agents in aqueous solvents. As used herein, the term "spray" refers to a liquid minutely divided as by a jet of air or steam. Nasal spray drug products contain therapeutically active ingredients dissolved or suspended in solutions or mixtures of excipients in nonpressurized dispensers. As used herein, the term "metered spray" refers to a non-pressurized dosage form consisting of valves that allow the dispensing of a specified quantity of spray upon each activation. As used herein, the term "suspension spray" refers to a liquid preparation containing solid particles dispersed in a liquid vehicle and in the form of course droplets or as finely divided solids.

IV. Kits for Treating or Preventing Mucositis

Another aspect of the invention is a kit for treating or preventing mucositis. The kits of the invention are useful for storing and dispensing compositions of the invention. The kits comprise one or more doses of the composition of the invention, and one or more additional components selected from: a mucoadministration device, a mixing chamber, a diluent, and/or printed instructions for carrying out one or more of the methods described herein. In one embodiment, the kit comprises two of the foregoing additional components. In another embodiment, the kit comprises three of the foregoing additional components. In another embodiment, the kit comprises four of the foregoing additional components. In some embodiments, the mucoadministration device is empty, or contains a diluent to which the composition can be added. In other embodiments, the mucoadministration device contains one or more doses of the composition in solid (e.g., powder), liquid, or semi-solid form, thereby functioning as the pre-filled container.

In some embodiments, the kit includes a mucoadministration device. In some embodiments, the mucoadministration device contains one or more doses of the composition of the invention. In some embodiments, the kit includes instructions for carrying out one or more methods, such as a method for treating or preventing mucositis (e.g., CRS) comprising mucoadministering a composition of the invention to a subject in need thereof.

It should be appreciated that the kits of the invention are not limited to any particular container configuration. The container(s) can be constructed and arranged, and the composition can be prepared (e.g., solid or liquid), stored, and dispensed, in any of numerous ways within the scope of the invention. For example, in some embodiments, the kit includes a tray or other housing with one or more cavities of desirable geometries for receiving one or more components of the kit. Containers for holding components of the kit can be rigid (such as canisters) or soft (such as bags or pouches), as needed or desired. Materials for constructing containers for medicaments in various physical states are known in the art. In some embodiments, the container(s) and housing is plastic, such as polypropylene. The kit is preferably packaged for ease of handling and use by the subject to be treated or by medical personnel. The kit is preferably sealed and sterilized.

The kit may contain one or more containers of the composition. Each container may contain one or more doses of the composition. Preferably, each kit contains multiple doses of the composition effective for treatment or prevention of mucositis in a human subject.

Preferably, the composition of each kit is present in one or more pre-filled containers, such as packets or sachets. In some embodiments, one or more dosages of the composition in liquid or solid (e.g., powder) form are packaged in one or more foil laminate sachets.

The invention will be further described in the following examples, which are not meant to limit the scope of the invention in any way.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Clinical Study

One hundred and fifty human subjects suffering from surgery-refractory chronic rhinosinusitis (CRS) were studied to evaluate the efficacy of intranasal amphotericin B compared to a composition of the invention, Formulation 1, in treating the disorder.

A sachet of the composition of the invention in powder form was prepared and reconstituted with sterile water prior to mucoadministration. Sachet fill weight was 1.54 grams, and was reconstituted in 58.5 ml sterile water. The ingredients of Formulation 1 are listed in Table 2 below.

TABLE 2

| Formulation 1 | |
| --- | --- |
| Ingredient | % w/w |
| Sodium Phosphate Dibasic, Anhydrous, USP | 1.59 |
| Sodium Phosphate Monobasic, Anhydrous, USP | 0.96 |
| Calcium Carbonate, USP | 0.015 |
| FD&C Yellow #5, Lake (15%) | 0.0015 |
| Sterile Water | QS |

The patients were administered about 20 mL of Formulation 1 per nostril (approximately one to three sprays per nostril), two to four times daily for at least three months.

Diagnostic analysis showed that the patients had the following criteria prior to the study: (1) symptoms with a duration of greater than 12 weeks; (2) presence of observable disease within the nasal-paranasal anatomy as evidenced by a CT scan, (e.g., at least 5 mm mucosal thickening in at least 1 maxillary sinus at the level of the middle meatus); (3) endoscopy to exclude presence of polyps that are stage 4 in middle meatus and document presence of inflammation, such as polypoid thickening of the mucosa, discolored mucus or edema of the middle meatus or ethmoid area; and optionally (4) a history of at least 1 prior maxillary sinus surgery for CS consisting of antrostomy with or without polypectomy greater than or equal to 6 months prior to randomization.

In addition to patient interviewing, CT scan analysis, visual examination, and fungal culture analysis, two types of evaluations were used to score the success of the treatment: an endoscopic evaluation and a patient symptom evaluation. These evaluations were scored as follows:

Endoscopic Evaluation Stage 0: no evidence of disease; Stage 1: polypoid changes/polyps seen by endoscopy only; Stage 2: polyps in the middle meatus; Stage 3: polyps filling the nasal cavity. Patient Symptom Evaluation Stage −2: very bad/much worse; Stage −1: bad/worse; Stage 0: baseline/no change; Stage 1: good/improved; Stage 2: very good/free of symptoms.

Analysis of the data from the blinded trial demonstrated that the exemplary compositions of the invention provided an improvement in polyposis by endoscopy.

Analysis of the data from the blinded trial demonstrates that the compositions are non-irritative and can be used to effectively treat non-invasive fungus-induced rhinosinusitis.

Human subjects suffering from surgery-refractory chronic rhinosinusitis (prior endoscopic sinus surgery) were instructed to store the formulation in sachets in the refrigerator and sterile water was stored at room temperature. Reconstituted material was used within two hours of reconstitution. After reconstitution, material was withdrawn from the bottle into a nasal syringe bearing a flexible silicone tip for administration to each nostril. A uniform suspension was drawn into the syringe. To accomplish this, the patient withdrew approximately 25 ml of the composition into the syringe, emptied the syringe by depressing the plunger while maintaining the syringe tip inside of the bottle, and then withdrew a 20 ml dose using the markings on the syringe. The "withdraw, empty, withdraw" syringe filling method was employed each time the composition was used. The syringe provided a measured dose applied to the nose with pressure. Patients were instructed to point the tip of the syringe toward the middle meatus region and tilt the head to the side being irrigated. Two (20 ml) aliquots were administered in the morning (20 ml per nostril) and 2 (20 ml) aliquots at night (20 ml per nostril) for 16 weeks.

Patients came to the study site for a series of evaluations. Study procedures that were conducted included the following:

Reviewing inclusion/exclusion criteria;
Obtaining IC;
Collecting demographic data and medical history data;
Conducting the individual patient interview facilitating discussion of patients' defining CS symptoms;
Documenting the patient's concomitant medication usage;
Administering the patient's Global Rating Assessment of Symptom Status;
Administering the physician Global Rating Assessment of Symptom Status;
Performing a brief physical examination;
Administration of the RhinoQoL Survey (FIGS. 1A-1E).
Patients who discontinued after screening did not contribute to the symptom interview.

Demographic data was collected during the individual patient interviews. Medical history data was collected and recorded. A brief physical examination was conducted and included general assessments performed in accordance with the investigator's examination scheme. Findings were recorded. Patients participated in individual interviews, the goal of which was to determine the symptoms of CS that the patients thought define the disease. This qualitative step within the current study served to frame the concepts and is a well-accepted form of identifying such concepts. The format of the interview was in individual sessions so as to address multiple important qualitative aspects of symptom identification, including:

the ability for clarification to patients if a concept or question is not understood;
the ability to ask patients to clarify a vague answer; and
the opportunity for interaction between patients and the interviewer that can lead to conceptualizations not previously considered.

Interviews were recorded and transcribed. Transcripts were subject to content analysis in which CS symptoms were identified and standardized. Physicians knowledgeable in the treatment of CS were involved in determination of symptoms as well as determining the cardinality of a given symptom.

As supplemental information, each patient was asked to rank order his or her CS symptoms in terms of that which is the most significant to him or her.

Rhinosinusitis Quality of Life Survey

The RhinoQoL is a self-administered, clinically relevant, internally consistent, valid and reliable measure of the severity of the sinusitis symptoms and their functional impact (Atlas Si et al., *Qual, Life Res.*, 2005, 14:1375-1386; Atlas S J et al., *Laryngoscope*, 2005, 115:846-854). The full tool, as well as the individual scales comprising the tool, have demonstrated clinically meaningful responsiveness to change and interpretability in patients with CS requiring surgery. Patients are instructed at the top of the questionnaire to respond to every item on the questionnaire and not to skip any items.

The RhinoQoL consists of 3 scales:

SBS (3 items: sinus headache, facial pain, facial pressure; blocked or stuffy nose; and postnasal drip).

Symptom frequency (5 items: sinus/headache, facial pain, facial pressure; blocked or stuffy nose; postnasal drip; thick nasal discharge; runny nose).

Symptom impact (9 items: tired or fatigued; trouble sleeping; hard to concentrate; harder to do things you normally do; embarrassed; frustrated; irritable; sad or depressed).

The full RhinoQoL questionnaire was administered to patients as the final assessment at the end of their study visit.

Patient Global Rating Assessment of Symptom Status

Each patient's assessment of his/her symptom status was assessed by asking this question, similar to that used by Atlas et al. in their validation of the RhinoQoL:

"In general, how would you rate your overall sinus/nasal symptoms now?" with the following choices of responses: "excellent," "very good," "good," "fair," or "poor."

Physician Global Rating Assessment of Symptom Status

The physician assessing patients answered a question similar to the Patient Global Rating Assessment of Symptom Status outlined above. This question was answered by the physician examining the patient and read:

"In general, how would you rate this patient's sinus/nasal symptoms now?" with the following choices of responses: "excellent," "very good," "good," "fair, or "poor."

A summary of the results of the study are shown in Table 3 (intent-to-treat population, n=150).

TABLE 3

Summary Data for Formulation 1

| Endpoint | Score at Baseline (mean) | Score at Week 16 (mean) | P-value |
|---|---|---|---|
| RhinoQOL Composite Scores (0-100%; lower = better; n = 150) | | | |
| Symptom Bothersomeness | 61.2 | 45.9 | P < 0.0001 |
| Symptom Intensity | 71.2 | 59.0 | P < 0.0001 |
| Symptom Frequency | 60.6 | 49.7 | P < 0.0001 |
| Cardinal Symptoms (CSS) (scale 0-5; lower = better; n = 150) | | | |
| Headache | 3.07 | 2.30 | P < 0.0001 |
| Congestion | 3.39 | 2.63 | P < 0.0001 |
| Endoscopy | 1.72 | 1.31 | P < 0.0001 |
| (scale 0-4; lower = better; n = 150) CT Scan (mucosal thickening) (scale 0-100%; lower = better) (n = 33) | | | |
| CT (right) | 67.5% | 56.8% | p < 0.002 |
| CT (left) | 68.7% | 57.7% | p < 0.004 |

Table 4, below, outlines the CT, endoscopy, CSS symptoms, RhinoQOL symptoms as measured in the 150-patient population.

TABLE 4

Formulation 1 - Changes from baseline to 16-weeks (population is Intent to Treat)

| Treatment | Variable | Description | n | Mean Value at Baseline | Mean Value at 16-weeks | Mean Change from Baseline | Std. Deviation of Change from Baseline | p-value of change from baseline | Correlation to Patient Global Rating | p-value | Correlation to Physician Global Rating | p-value |
|---|---|---|---|---|---|---|---|---|---|---|---|---|
| Formulation1 | ctR | CT(r) | 33 | 0.675 | 0.568 | −0.107 | 0.161 | 0.0017 | 0.231 | 0.195 | 0.346 | 0.0527 |
| Formulation1 | ctL | CT(l) | 33 | 0.687 | 0.575 | −0.112 | 0.197 | 0.00402 | 0.311 | 0.0777 | 0.233 | 0.199 |
| Formulation1 | eL | endoRight | 150 | 1.66 | 1.28 | −0.38 | 0.857 | $p < 0.01$ | 0.271 | 0.000778 | 0.404 | $p < 0.01$ |
| Formulation1 | eR | endoLeft | 150 | 1.77 | 1.35 | −0.427 | 0.958 | $p < 0.01$ | 0.155 | 0.0581 | 0.29 | $p < 0.01$ |
| Formulation1 | s1 | congestion | 150 | 3.39 | 2.63 | −0.767 | 1.42 | $p < 0.01$ | 0.584 | $p < 0.01$ | 0.464 | $p < 0.01$ |
| Formulation1 | s2 | cough | 150 | 1.99 | 1.44 | −0.547 | 1.58 | $p < 0.01$ | 0.384 | $p < 0.01$ | 0.347 | $p < 0.01$ |
| Formulation1 | s3 | dry mouth | 150 | 2.29 | 1.67 | −0.62 | 1.43 | $p < 0.01$ | 0.305 | $p < 0.01$ | 0.315 | $p < 0.01$ |
| Formulation1 | s4 | ear pain | 150 | 1.76 | 1.21 | −0.553 | 1.39 | $p < 0.01$ | 0.235 | $p < 0.01$ | 0.261 | $p < 0.01$ |
| Formulation1 | s5 | ear press | 150 | 2.22 | 1.57 | −0.653 | 1.53 | $p < 0.01$ | 0.402 | $p < 0.01$ | 0.316 | $p < 0.01$ |
| Formulation1 | s6 | face pain | 150 | 2.54 | 1.87 | −0.667 | 1.6 | $p < 0.01$ | 0.515 | $p < 0.01$ | 0.431 | $p < 0.01$ |
| Formulation1 | s7 | face press | 150 | 2.77 | 2.01 | −0.76 | 1.57 | $p < 0.01$ | 0.51 | $p < 0.01$ | 0.38 | $p < 0.01$ |
| Formulation1 | s8 | fever | 149 | 0.671 | 0.367 | −0.302 | 1.24 | $p < 0.01$ | 0.195 | 0.0174 | 0.235 | $p < 0.01$ |
| Formulation1 | s9 | headache | 150 | 3.07 | 2.3 | −0.767 | 1.65 | $p < 0.01$ | 0.596 | $p < 0.01$ | 0.417 | $p < 0.01$ |
| Formulation1 | s10 | anosmia | 150 | 3.03 | 2.27 | −0.753 | 1.51 | $p < 0.01$ | 0.277 | $p < 0.01$ | 0.275 | $p < 0.01$ |
| Formulation1 | s11 | nasal drip | 150 | 3.24 | 2.41 | −0.833 | 1.49 | $p < 0.01$ | 0.473 | $p < 0.01$ | 0.366 | $p < 0.01$ |
| Formulation1 | s12 | runny nose | 150 | 2.62 | 1.81 | −0.807 | 1.46 | $p < 0.01$ | 0.404 | $p < 0.01$ | 0.391 | $p < 0.01$ |
| Formulation1 | s13 | sneezing | 150 | 2.21 | 1.53 | −0.673 | 1.48 | $p < 0.01$ | 0.368 | $p < 0.01$ | 0.381 | $p < 0.01$ |
| Formulation1 | s14 | sore throat | 150 | 1.73 | 1.18 | −0.547 | 1.54 | $p < 0.01$ | 0.314 | $p < 0.01$ | 0.26 | $p < 0.01$ |
| Formulation1 | s15 | tired | 149 | 3.16 | 2.45 | −0.705 | 1.64 | $p < 0.01$ | 0.433 | $p < 0.01$ | 0.211 | 0.0106 |
| Formulation1 | s16 | watery eyes | 149 | 2.23 | 1.47 | −0.758 | 1.41 | $p < 0.01$ | 0.391 | $p < 0.01$ | 0.3 | $p < 0.01$ |
| Formulation1 | rq1 | freqHeadache-PainPress | 149 | 3.53 | 2.94 | −0.597 | 1.11 | $p < 0.01$ | 0.557 | $p < 0.01$ | 0.414 | $p < 0.01$ |
| Formulation1 | rq2 | stuffy nose | 150 | 3.66 | 3 | −0.66 | 1.19 | $p < 0.01$ | 0.468 | $p < 0.01$ | 0.44 | $p < 0.01$ |
| Formulation1 | rq3 | nasal drip | 149 | 3.49 | 2.91 | −0.591 | 1.1 | $p < 0.01$ | 0.474 | $p < 0.01$ | 0.468 | $p < 0.01$ |
| Formulation1 | rq4 | nasal discharge | 150 | 3.07 | 2.66 | −0.407 | 1.31 | $p < 0.01$ | 0.379 | $p < 0.01$ | 0.298 | $p < 0.01$ |
| Formulation1 | rq5 | runny nose | 150 | 2.85 | 2.38 | −0.473 | 1.17 | $p < 0.01$ | 0.443 | $p < 0.01$ | 0.496 | $p < 0.01$ |
| Formulation1 | rq6 | fatigue | 150 | 3.43 | 2.76 | −0.667 | 1.23 | $p < 0.01$ | 0.481 | $p < 0.01$ | 0.294 | $p < 0.01$ |
| Formulation1 | rq7 | insomnia | 150 | 2.95 | 2.4 | −0.547 | 1.1 | $p < 0.01$ | 0.447 | $p < 0.01$ | 0.391 | $p < 0.01$ |
| Formulation1 | rq8 | concentration daily | 150 | 3.04 | 2.47 | −0.573 | 1.14 | $p < 0.01$ | 0.521 | $p < 0.01$ | 0.33 | $p < 0.01$ |
| Formulation1 | rq9 | function | 150 | 2.95 | 2.41 | −0.547 | 1.17 | $p < 0.01$ | 0.466 | $p < 0.01$ | 0.387 | $p < 0.01$ |
| Formulation1 | rq10 | embarras | 150 | 2.57 | 2.05 | −0.52 | 1.07 | $p < 0.01$ | 0.344 | $p < 0.01$ | 0.333 | $p < 0.01$ |
| Formulation1 | rq11 | frustration | 150 | 3.55 | 2.84 | −0.707 | 1.27 | $p < 0.01$ | 0.584 | $p < 0.01$ | 0.454 | $p < 0.01$ |
| Formulation1 | rq12 | irritable | 150 | 3.13 | 2.53 | −0.6 | 1.18 | $p < 0.01$ | 0.488 | $p < 0.01$ | 0.44 | $p < 0.01$ |
| Formulation1 | rq13 | depressed | 150 | 2.31 | 1.9 | −0.407 | 1.09 | $p < 0.01$ | 0.307 | $p < 0.01$ | 0.35 | $p < 0.01$ |
| Formulation1 | rq14 | think of symptoms | 150 | 3.53 | 2.95 | −0.587 | 1.14 | $p < 0.01$ | 0.583 | $p < 0.01$ | 0.523 | $p < 0.01$ |
| Formulation1 | sbs | SBS | 149 | 61.2 | 45.9 | −15.2 | 26.8 | $p < 0.01$ | 0.603 | $p < 0.01$ | 0.474 | $p < 0.01$ |
| Formulation1 | sis | SIS | 148 | 71.2 | 59 | −12.4 | 18.2 | $p < 0.01$ | 0.582 | $p < 0.01$ | 0.523 | $p < 0.01$ |
| Formulation1 | sfs | SFS | 150 | 60.6 | 49.7 | −10.9 | 17.5 | $p < 0.01$ | 0.613 | $p < 0.01$ | 0.528 | $p < 0.01$ |
| Formulation1 | prate | Pt. Global Rate | 150 | 3.41 | 2.74 | −0.673 | 1.08 | $p < 0.01$ | 1 | $p < 0.01$ | 0.566 | $p < 0.01$ |
| Formulation1 | mdrate | Phys Global Rate | 147 | 3.01 | 2.28 | −0.741 | 1.19 | $p < 0.01$ | 0.566 | $p < 0.01$ | 1 | 0 |
| Formulation1 | eMBP | eMBP | 79 | 1330 | 3630 | 2510 | 13400 | 0.0155 | 0.0737 | 0.519 | −0.0109 | 0.925 |

Legend:
rq* values: RhinoQOL (scale 1-5, lower = better)
s* values: CSS symptoms (scale 1-5, lower = better)
ct* values: left and right CT occlusion values (from 0-100%; lower = better)
sbs, sis, sfs: Symptom Bothersomeness, Intensity, and Frequency (scale = 0-100; lower = better)

The per-nostril CT values are demonstrated for a subject of patients (n=33) for which per-nostril CT values could be obtained following completion of the study. Variables measured included the following:
rq* values: RhinoQOL (scale 1-5, lower=better);
s* values: CSS symptoms (scale 1-5, lower=better);
ct* values: left and right CT occlusion values (from 0-100%; lower=better) sbs, sis, sfs:
Symptom Bothersomeness, Intensity, and Frequency (scale=0-100; lower=better).

For each variable measured, the mean value at baseline and following 16-weeks of control solution administration are showed, as are the mean changes (lower changes or negative changes denote improvements from baseline to 16 weeks). Also provided are the standard deviation of the change from baseline as measured in treated subjects, and a p-value calculated using a two-sided paired Wilcoxon rank-sum test (Mann-Whitney test) denoting the statistical significance of changes from baseline to 16-weeks. Also listed in Table 4 are the Spearman product-momen correlation coefficient (rho) between the individual symptom improvements and the improvement in both physician and patient-reported global symptoms ratings ("Patient Global Rating" and "Physician Global Rating").

Positive coefficients denote a positive correlation, and correlations coefficients exceeding 0.5 denote a strong positive correlation. P-values are computed using algorithm AS 89 using the R statistical computing package.

In all subjective symptoms measured in the 150-patient study, subjects demonstrated strong statistically-significant improvement from baseline to 16-weeks following administration of the Formulation 1 lavage. Patients had statistically-significant improvements in per-nostril endoscopy scores as well as improvements in per-nostril CT that trended towards statistical significance (p<0.053). Patients also reported statistically-significant positive correlations with improvements in patient- and physician-global quality-of-life scores. The results herein demonstrate a clear clinical benefit.

Formulation 1 was tested in vitro for antifungal activity against *Alternaria alternate* with negative results.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A kit for treating mucositis, comprising a composition consisting essentially of sodium phosphate buffer and calcium carbonate, and at least one component selected from the group consisting of: a mucoadministration device, a mixing chamber, and a diluent.

2. The kit of claim 1, wherein said composition is packaged in one or more foil-wrapped sachets.

3. The kit of claim 1, wherein said composition is a solid.

4. The kit of claim 3, wherein said solid is a powder.

5. The kit of claim 1, wherein said composition is a liquid.

6. The kit of claim 1, wherein the kit comprises said diluent, and wherein said diluent comprises water.

7. The kit of claim 1, wherein said composition consists essentially of sodium phosphate dibasic, sodium phosphate monobasic, and calcium carbonate.

8. The kit of claim 1, wherein said composition has about 2% to about 3% (w/w) sodium phosphate buffer and about 0.005 to about 0.030% (w/w) calcium carbonate.

9. The kit of claim 1, wherein said composition has about 1.59% (w/w) sodium phosphate dibasic, about 0.96% (w/w) sodium phosphate monobasic, and about 0.015% (w/w) calcium carbonate.

10. The kit of claim 1, wherein said composition does not include any anti-fungal agent.

11. The kit of claim 1, wherein the kit comprises said mucoadministration device, said mixing chamber, and said diluent.

12. The kit of claim 1, wherein said mucoadministration device is selected from the group consisting of a nasal pump sprayer, nasal irrigator, syringe, and nebulizer.

13. The kit of claim 1, wherein the kit comprises said mucoadministration device.

14. The kit of claim 13, wherein said mucoadministration device is a nasal irrigator.

15. The kit of claim 14, wherein said nasal irrigator has an outlet portion made of a flexible material, and said outlet portion is adapted to seal a subject's nostril during mucoadministration.

16. The kit of claim 15, wherein said flexible material is silicone.

17. A kit for treating mucositis, comprising a composition comprising sodium phosphate buffer and calcium carbonate, and at least one component selected from the group consisting of: a nasal irrigator, a mixing chamber, and a diluent, wherein said composition includes no additional active agents.

18. The kit of claim 1, wherein said composition is a powder packaged in one or more packets or sachets.

19. The kit of claim 17, wherein said composition is a powder packaged in one or more packets or sachets.

* * * * *

UNITED STATES PATENT AND TRADEMARK OFFICE
CERTIFICATE OF CORRECTION

| | | |
|---|---|---|
| PATENT NO. | : 8,940,319 B2 | Page 1 of 1 |
| APPLICATION NO. | : 13/486197 | |
| DATED | : January 27, 2015 | |
| INVENTOR(S) | : Francis E. O'Donnell and Angelos M. Stergiou | |

It is certified that error appears in the above-identified patent and that said Letters Patent is hereby corrected as shown below:

In the Specification

Column 12,
Line 39, "*Cunninahamelk*" should read --*Cunninahamella*--.

Column 20,
Line 5, "(Atlas Si et al." should read --(Atlas SJ et al.--.

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,940,319 B2  
APPLICATION NO. : 13/486197  
DATED : January 27, 2015  
INVENTOR(S) : Francis E. O'Donnell and Angelos M. Stergiou Page 1 of 1

It is certified that error appears in the above-identified patent and that said Letters Patent is hereby corrected as shown below:

On the Title Page

Item "(73) Assignee: Accentia Biopharmceuticals, Inc., Tampa, FL (US)"  
Should read:  
--(73) Assignee: Pabeti, Inc., Marion, IL (US)--

Signed and Sealed this  
Sixth Day of August, 2019

Andrei Iancu  
*Director of the United States Patent and Trademark Office*